United States Patent [19]

Kaali et al.

[11] Patent Number: 4,932,421
[45] Date of Patent: Jun. 12, 1990

[54] ELECTRIFIED INTRAUTERINE DEVICE

[76] Inventors: Steven Kaali, 88 Ashford Ave., Dobbs Ferry, N.Y. 10522; Peter M. Schwolsky, 4101 Cathedral Ave., NW., Washington, D.C. 20016

[21] Appl. No.: 300,413

[22] Filed: Jan. 23, 1989

[51] Int. Cl.$^5$ .................. A61F 13/00; A61F 5/00
[52] U.S. Cl. ............................ 128/831; 128/833; 128/839
[58] Field of Search .................. 128/831–841, 128/783, 775, 784, 788; 604/891; 429/16 C

[56] References Cited

U.S. PATENT DOCUMENTS

| | | | |
|---|---|---|---|
| 454,573 | 6/1891 | Sherman | 128/788 |
| 527,788 | 10/1894 | Hebard | 128/788 |
| 3,777,748 | 12/1973 | Abramson | 128/840 |
| 3,866,613 | 2/1975 | Kenny | 128/788 |
| 3,918,444 | 11/1975 | Hoff | 128/840 |
| 4,026,281 | 5/1977 | Mayberry | 128/840 |
| 4,031,365 | 6/1977 | Raggiotti | 128/738 |
| 4,561,433 | 12/1985 | Wheeler | 128/840 |
| 4,616,640 | 10/1986 | Kaali | 128/833 |
| 4,724,832 | 2/1988 | Strubel | 128/840 |
| 4,770,167 | 9/1988 | Kaali | 128/833 |

Primary Examiner—Robert A. Hafer
Assistant Examiner—Michael Brown
Attorney, Agent, or Firm—Charles W. Helzer

[57] ABSTRACT

An electrified intrauterine device (IUD) is provided which has an IUD body member fabricated from materials which are physiologically compatible with human tissue and fluids and physically proportioned to be placed and retained within the uterus of a female mammal. Spaced-apart electrically conductive electrodes are formed on the IUD body member from electrically conductive materials that are physiologically compatible with human tissue and fluids. Self-contained electric batteries are supported within the IUD body member that forms a sealed outer casing of biologically inert material compatible with human tissue and fluids. The batteries are capable of producing an electromotive force of known voltage and current rating and are of a size to be inserted and retained within the uterus of a female mammal. The device is completed by electrically conductive interconnecting conductors between respective opposite polarity terminals of the batteries and respective ones of the spaced-apart electrically conductive electrodes on the IUD body member whereby an electric field force can be established and maintained within the uterus of a female mammal in which the electrified IUD is inserted.

21 Claims, 2 Drawing Sheets

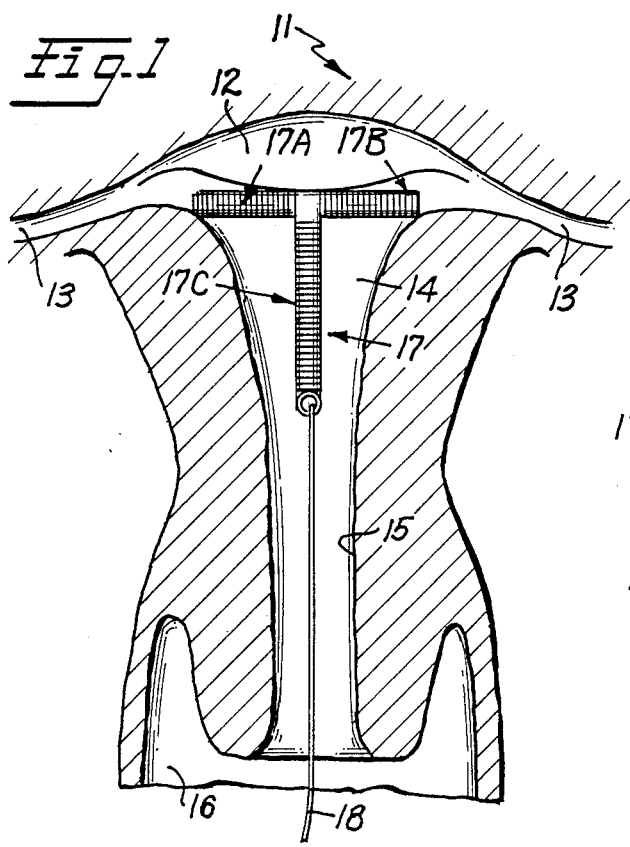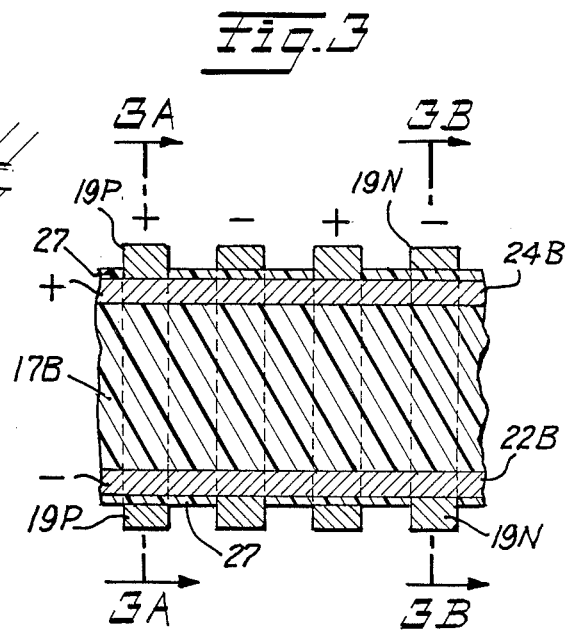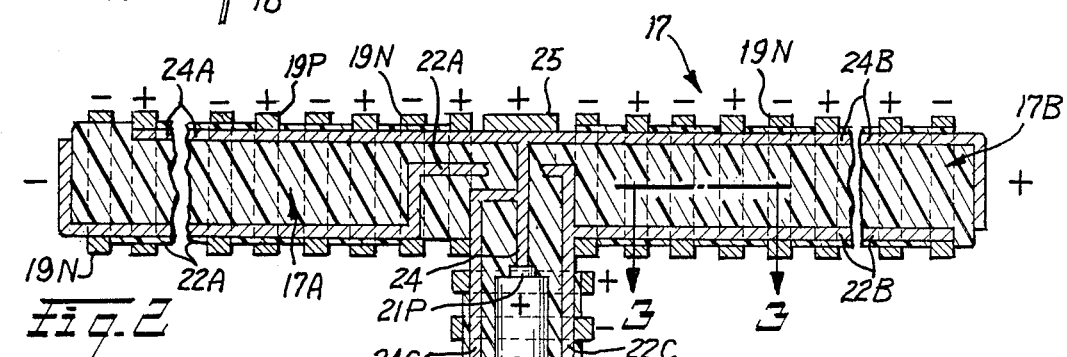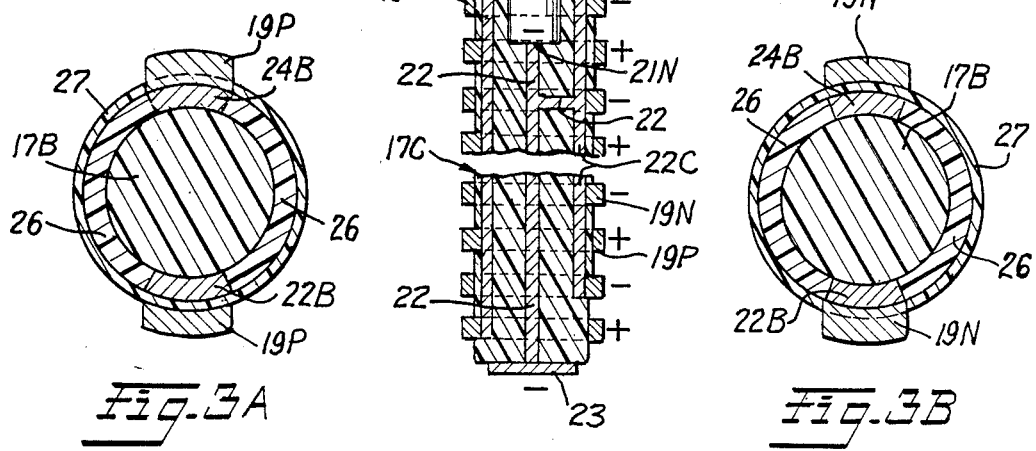

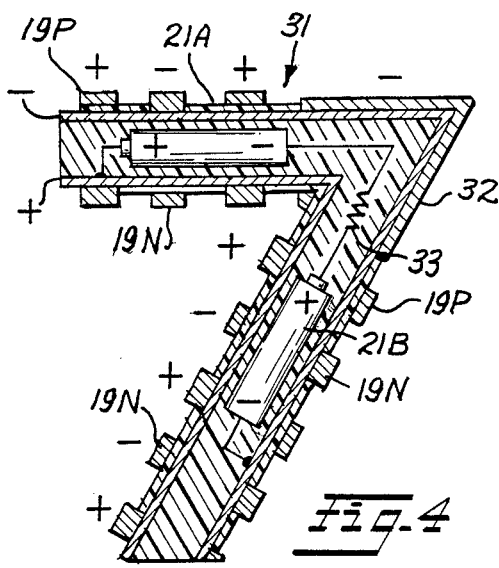
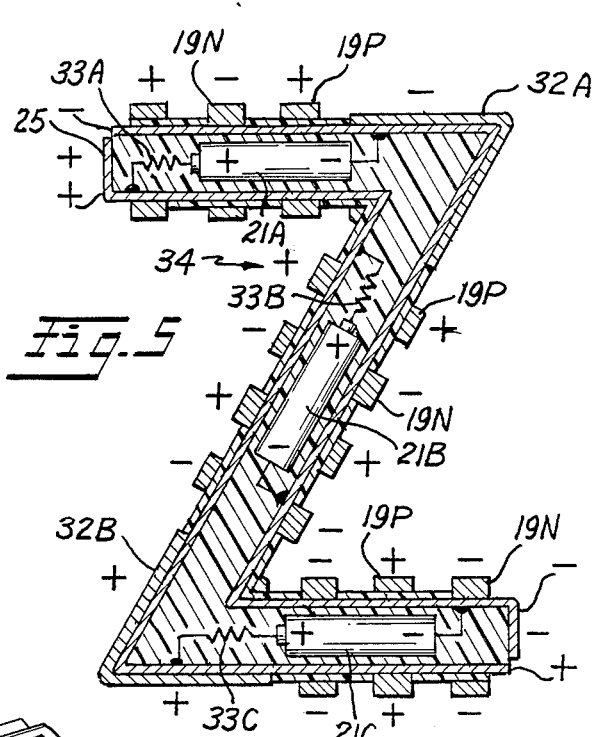
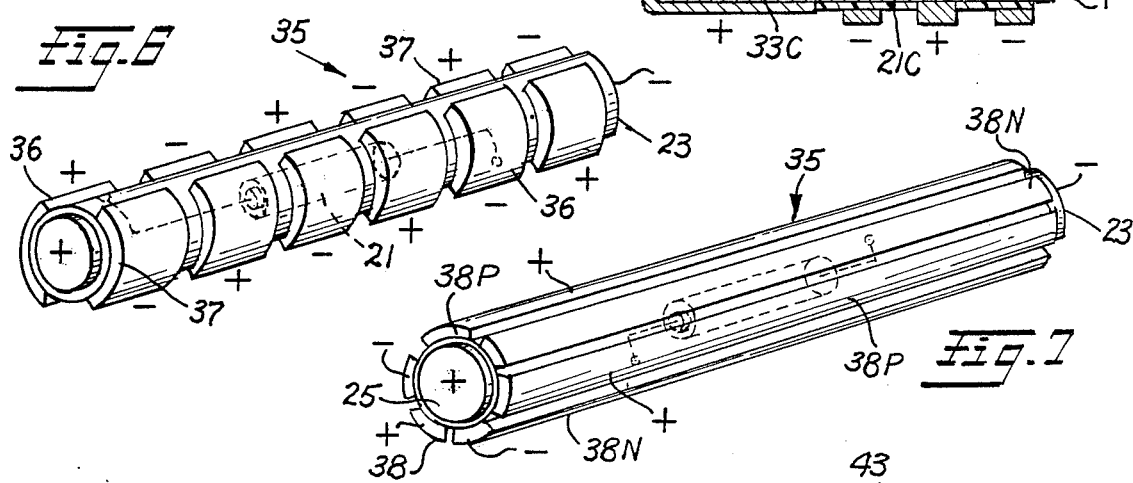
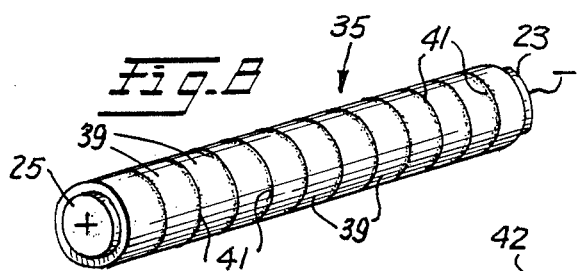
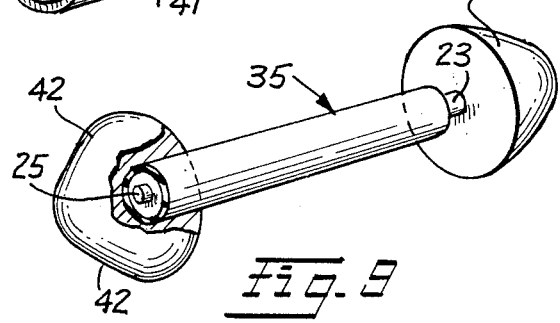
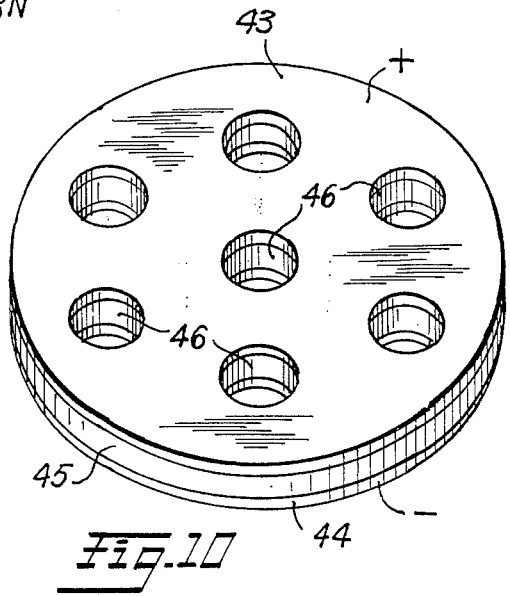

ELECTRIFIED INTRAUTERINE DEVICE

FIELD OF INVENTION

This invention relates to the field of contraceptive devices for female mammals.

More particularly, the invention relates to contraceptives of the intrauterine device (IUD) type and to a novel electrified IUD especially.

BACKGROUND OF INVENTION

U.S. Pat. No. 4,616,640 for a "Birth Control Method and Device Employing Electric Forces" - issued Oct. 14, 1986 - Steven Kaali, Peter M. Schwolsky and Joseph W. Porter -inventors discloses a novel method and device using electric field forces within or about the cervical canal of a female mammal for acting on sperm and preventing migration of the male sperm through the cervical canal into the uterine cavity where it might fertilize an egg.

U.S. Pat. No. 4,770,167 for an "Electrical, Generally Rounded Resilient, Canopy-Like Contraceptive Devices" - issued Sept. 13, 1988 to Steven Kaali and Peter M. Schwolsky - inventors discloses and claims electrified contraceptive devices of the diaphragm and/or cervical cap type wherein electrical forces generated within the device augment the contraceptive action of either a diaphragm or a cervical cap.

U.S. patent application Ser. No. 141,132 filed Jan. 6, 1988 for an "Electrified Vaginal Ring", Steven Kaali and Peter M. Schwolsky, inventors, discloses and claims an electrified vaginal ring for use as a contraceptive device for birth control purposes.

SUMMARY OF INVENTION

The present invention makes available to the medical profession and the consuming public an electrified IUD for use as a contraceptive device for birth control purposes.

In practicing the invention, an electrified intrauterine device (IUD) is provided which comprises an IUD body member fabricated from materials which are physiologically compatible with human tissue and fluids and physically proportioned to be placed and retained within the uterus of a female mammal. Spaced-apart electrically conductive electrodes are formed on the IUD body member from electrically conductive materials that also are physiologically compatible with human tissue and fluids. Self-contained electric batteries are supported within the IUD body member or other sealed outer casing of biologically inert material compatible with human tissue and fluids. The batteries are capable of producing an electromotive force of known voltage and current rating and are of a size to be inserted and retained within the uterus of a female mammal. The device is completed by electrically conductive conductors interconnected between respective opposite polarity terminals of the battery means and respective ones of the spaced-apart electrically conductive electrode means on the IUD body member whereby an electric field force can be established and maintained within the uterus of a female mammal in which the electrified IUD is inserted.

In preferred embodiments of the electrified intrauterine device, the batteries are embedded or contained in the IUD member and the IUD body member is formed from electrically insulating material. Both the IUD body member and the spaced-apart electrodes formed on its exterior surface are comprised by electrically conductive pathways deposited or otherwise formed on the exterior of the insulating IUD body member surface. In all embodiments of the invention, a string or other similar strand of material such as a monofilament plastic cord is secured to the IUD body member and upon implantation of the device in the uterus of a female mammal extends out of the uterus and the vaginal canal so that the IUD body member readily can be extracted.

In addition to its function as an antispermicide as described above, it is believed that the electrified IUD also serves an antibacterial, an antifungal and anti-viral function as disclosed in the above-noted U.S. Pat. Nos. 4,616,640; 4,770,167 and U.S. patent application Ser. No. 141,132.

BRIEF DESCRIPTION OF DRAWINGS

These and other objects, features and many of the attendant advantages of this invention will be appreciated more readily as the same becomes better understood from a reading of the following detailed description when considered in connection with the accompanying drawings, wherein like parts in each of the several figures are identified by the same reference characters and wherein:

FIG. 1 is partial schematic view of the reproductive organs of a human female and shows an electrified IUD constructed according to the present invention secured within the uterine cavity which serves as a contraceptive for birth control purposes;

FIG. 2 is an enlarged elevational view of the electrified IUD shown in use in FIG. 1 of the drawings;

FIG. 3 is an enlarged sectional view of segment 3—3 of the electrified IUD shown in FIG. 2;

FIGS. 3A and 3B are cross sectional views taken through respective planes 3A—3A and 3B—3B of FIG. 3;

FIG. 4 is a plan view of a second embodiment of the invention wherein the electrified IUD body member is in the shape of a 7 and which employs two embedded batteries connected in series circuit relationship through a current limiting resistor to provide larger voltage electric field forces to the electrified IUD;

FIG. 5 is a plan view of still a third embodiment of the invention which makes available a Z-shaped IUD body member having three embedded batteries connected in parallel circuit relationship to conductive electrodes on the exterior of the Z-shaped. IUD body member whereby increased current and reliability during the operation is provided in cases of failure of any one of the parallel connected batteries;

FIG. 6 is a perspective view of still another embodiment of the invention wherein the IUD body member is in the shape of an elongate cylinder having annular ring electrodes formed around its surface;

FIG. 7 is a perspective view of still another embodiment of the invention employing an elongated cylinder-shaped IUD body member having the exterior electrodes extending longitudinally along the elongate axis of the IUD body member;

FIG. 8 is a perspective view of still another elongate cylinder-shaped IUD body member which employs a plurality of button-shaped electromotive cells physically connected in series electrical circuit relationship by means of a conductive adhesive that secures the button-shaped cells together in a unitary elongate cylindrical form;

FIG. 9 is a perspective view of still another embodiment of electrified IUD according to the invention employing an elongated cylindrical-shaped body member having mushroom-shaped conductive electrodes secured to each of its ends to assure good contact and the formation of strong electric field forces when implanted within the uterine cavity; and FIG. 10 is perspective view of a disc-type IUD body member formed by a battery that is fabricated in the shape of a coin having through passageways through its opposite flat surfaces in order to provide drainage passageways for fluids upon the electrified IUD being implanted in the uterine cavity of a female mammal.

BEST MODE OF PRACTICING THE INVENTION

FIG. 1 is a partial schematic view of the reproductive organs 11 of a female human comprised by the uterus 12, the fallopian tubes 13, the uterine cavity 14, the cervical canal 15 (also referred to as the cervix) and the vagina 16. A Tee-shaped electrified IUD 17 is retained in place within the uterine cavity with the cross arms of the Tee extending across the upper portion of the uterine cavity and with the shank portion of the Tee-shaped device extending downwardly towards the cervical canal. To facilitate removal of the device, a string or cord 18 is secured to the lower end of the shank portion of the IUD with the string extending downwardly through the cervical canal and out through the vagina.

As best shown in FIG. 2 of the drawings, the Tee-shaped IUD body member 17 is fabricated from plastic, silicon, rubber or other suitable medical grade material which is known to be electrically insulating and biologically compatible with human tissue and fluids and is physically proportioned to be placed and retained within the uterus of a female mammal. The IUD body member 17 has a plurality of spaced-apart, electrically conductive electrode means in the form of parallel, annular conductive bands 19 formed about each of the arms 17A and 17B as well as the shank portion 17C of the Tee-shaped body member 17. The conductive electrodes 19 are formed by parallel, spaced-apart annular bands or rings of conductive material that can be grown, sputtered, electrodeposited or otherwise formed around each of the arm portions 17A and 17B and the shank portion 17C as best seen in FIG. 2. The annular conductive rings 19 are electrically isolated one from the other for a reason that will become clearer from the following description.

A self-contained electric battery means 21 is contained within the body of the shank portion 17C of the Tee-shaped IUD body member. Battery 21 preferably is within its own sealed outer casing of biologically inert material compatible with human tissue and fluids and is capable of producing an electromotive force of known voltage and current rating. Battery 21 preferably is embedded, molded or otherwise contained within the shank portion 17C of the Tee-shaped IUD body member but if desired could be inserted and separately retained within the uterus of a female mammal separately along with the IUD body member 17.

In order to provide the electric potential developed by the battery 21 to the various annular, conductive band electrodes 19, electrically conductive interconnecting pathway conductor means are formed along surfaces of the Tee-shaped IUD body member 17 as best shown in FIGS. 2, 3, 3A and 3B of the drawings. Referring to FIG. 2, a first conductive pathway 22 is provided between the negative terminal 21N of battery 21 and extends down to and contacts a flat circular electrode surface 23 formed on the exterior lower end of the shank portion 17C of the Tee-shaped IUD body member 17. A portion of the conductive pathway 22 extends over to a parallel conductive pathway 22C that is formed just under the outer surface of the shank portion 17C as will be described more fully hereinafter with relation to FIGS. 3, 3A and 3B or the drawings. The conductive pathway 22C runs entirely up the shank portion 17C of the Tee-shaped IUD body member to the intersection of the arm portions 17A and 17B where it then branches out into a pathway portion 22B that extends along the under surface of the arm portion 17B and to a portion 22A that extends to the left along the under surface of the arm portion 17A of the Tee-shaped IUD body member 17. Similarly, the positive terminal 21P of battery 21 is connected to a conductive pathway 24 that branches into corresponding pathways 24A, 24B and 24C. In addition, the conductive pathway 24 extends out to and contacts a positive polarity circular disc contact 25 formed at the head of the Tee-shaped IUD body member where the arms 17A and 17 B join the shank portion 17C.

The manner in which the conductive pathway runs 22A, 22B and 22C as well as 24A, 24B and 24C are insulated one from the other and are interconnected to the respective positive polarity, exterior conductive bands 19P and negative polarity, exterior conductive bands 19N, is best shown in FIGS. 3, 3A and 3B of the drawings. The Tee-shaped IUD body member 17 comprised by the shank portion 17C and the two arm portions 17A and 17B preferably are formed from a silicon-based plastic composition of medical grade quality and electrically insulating.

A segment of the arm portion 17B taken through planes 3—3 of FIG. 2 is shown in FIG. 3. The arm portion 17B as well as 17A and 17C preferably are circular in cross section as shown in FIGS. 3A and 3B. In fabricating the device, the conductive pathway runs 22B and 24B are formed along diametrically opposite lower and upper sides of the arm portion 17B by well known electronic miniaturized micro-circuit fabrication techniques with the intervening circumferential spaces between the two runs 22B and 24B being filled with an inner insulating layer 26. A second, outer insulating layer 27 is formed over the exposed upper surfaces of the first insulating layers 26 as well as under alternate ones of the plurality of parallel, spaced-apart conductive electrode rings 19N and 19P. This is achieved during fabrication of the device by appropriate masking of the exposed surfaces of the conductive pathway runs 22B and 24B.

Thereafter, the plurality of parallel, spaced-apart conductive electrodes 19P and 19N'' are deposited circumferentially surrounding the cross arm portions 17A and 17B and the shank portion 17C of the IUD body member 17. The resulting cross sectional structure is best seen in FIGS. 3A and 3B. FIG. 3A is a cross sectional view taken through plane 3A—3A of FIG. 3 wherein it will be seen that due to the openings in the mask used during the formation of the outer insulating layer 27, conductive electrode material 19P extends all the way down to and contacts the positive polarity conductive pathway run 24B of cross arm 17B. The same conductive electrode ring, however, on the underside of arm 17B is insulated from the negative polarity conductive pathway run 22B by the intervening outer insulating layer 27. In a similar fashion, in the case of the negative polarity conductive electrode rings 19N, as shown in FIG. 3B of the drawings, the masked opening provided during the formation of the outer insulating ring 27 allows the conductive electrode ring 19N material to extend down and contact the negative polarity conductive pathway run 22B; however, the interposition of the outer insulating layer 27 prevents the 19N ring electrode from contacting the upper positive polarity conductive pathway run 24B.

FIG. 4 is a plan view of an alternative embodiment of the invention wherein an IUD body member 31 is in the shape of a seven (7-shaped). In FIG. 4, the 7-shaped IUD body member 31 is again fabricated from electrically insulating plastic material which is biologically compatible with human tissue and fluids. A plurality of parallel, spaced-apart, electrically conductive ring electrodes 19N, 19P surround each of the respective arms of the 7-shaped IUD body member In addition, a generally V-shaped exterior electrode covers the juncture of the two arms of the 7-shaped member and constitutes one of the electric field producing electrodes of the device. Similar to the FIG. 2 embodiment of the invention, alternate ones of the ring-shaped electrodes 19N are supplied with a negative polarity excitation potential and interspersed between them are the positive polarity exterior ring electrodes 19P. Electric potentials are supplied to the respective ring electrodes 19N and 19P from a set of two batteries 21A and 21B which are electrically connected in series circuit relationship through a voltage limiting resistor 33 and connected through conductive pathways, similar to the pathways 22 and 24 used in the FIG. 2 embodiment of the invention, to the respective outer conductive ring electrodes 19N and 19P and 32. The batteries 21A and 21B are contained within a biologically inert material that is compatible with human tissue and fluids and are embedded within the respective arms of the 7-shaped IUD body member. By connecting two or more batteries in series circuit relationship in the manner shown through properly designed limiting resistors 33 fabricated using monolithic integrated circuit fabrication techniques, it is possible to increase the value of the electric potentials applied to the exterior ring-like electric field producing electrodes 19P and 19N thereby increasing the electric field forces produced within the uterine cavity.

FIG. 5 is a plan view of still a third embodiment of the invention which employs a Z-shaped IUD body member which is constructed in the same manner as the Tee-shaped IUD shown in FIG. 2 as well as the 7-shaped IUD shown in FIG. 4. The FIG. 5 device differs however in that it employs two V-shaped exterior electrode members 32A and 32B at the respective upper juncture of the upper flat arm of the Z with the diagonally extending leg of the Z and a lower V-shaped exterior electrode member 32B at the juncture of the diagonally extending leg of the Z with the lower flat arm of the Z. In addition, circular round electrodes of electrically conductive material are shown at 23 and 25 at the free ends of each of the lower and upper arms of the Z-shaped IUD body member. Lastly, it will be seen that the Z-shaped device is designed to employ three batteries 21A, 21B and 21C which are connected in parallel circuit relationship across the respective sets of alternate polarity, exterior, parallel, spaced-apart conductive ring electrodes 19P and 19N as well as the V-shaped electrodes 32A and 32B by means of the respective electrically conductive pathways 22, 23 and 24 similar to the corresponding conductive pathways employed and described with relation to the Tee-shaped body member shown in FIG. 2. By connecting the embedded batteries 21A, 21B and 21C in parallel in the manner shown, in the event of failure of any one of the batteries, at least two other batteries will still be active to provide electric field forces for the electrified IUD device.

In operation, the electrified IUD devices shown in FIGS. 2, 4 and 5 all function essentially in the same manner to produce electrical force fields within the uterine cavity to impede movement of male sperm and prevent them from landing upon and fertilizing an egg should one be present in the uterus. The manner in which the electric field forces act upon the sperm and impede its motion are still not fully understood, but are described in greater detail in the above-noted U.S. Pat. No. 4,616,640, the disclosure of which hereby is incorporated into the disclosure of this application in its entirety.

FIG. 6 of the drawings illustrates still a different embodiment of the invention wherein the electrified IUD body member is in the form of an elongated cylinder 35. The size and shape of the IUD body member 35 may be not too different from that of a standard, commercially available AA or AAA battery, but having a much smaller diameter. If desired, the elongated cylindrical body member 35 could be provided with alternate parallel, spaced-apart, conductive ring electrodes such as those illustrated on the arms of the embodiments of the electrified IUD device shown in FIGS. 2, 4 and 5. Such a construction would be quite simple and relatively inexpensive to manufacture. However, in the FIG. 6 embodiment the ring electrodes are split down each side and separated to provide opposing semi-circular band halves 36 and 37 with each pair of band halves being axially separated from the adjacent set of band halves along the elongate axis of the cylindrical IUD body member as shown in FIG. 6. In addition to the axially arrayed semi-circular band half electrodes 36 and 37, circular-shaped electrically conductive electrode members 23 and 25 are formed at each of the ends of the elongated cylindrically shaped IUD body member 35. A suitable battery such as shown at 21 is secured within the interior of the elongated cylinder body member 35 and suitable electrically conductive pathway runs (not shown) are provided so that alternate polarity electric potentials are provided to each one of the respective sets of spaced-apart, semi-circular band halves comprising the outer electric field emanating electrodes of the electrified IUD device. By constructing the device in this manner, a somewhat more uniform distribution of the electric field forces within the uterus can be accomplished around the electrified IUD device.

FIG. 7 of the drawings illustrates an embodiment of the invention which is somewhat similar to that shown in FIG. 6 with the exception that in FIG. 7 elongated strip-like, conductive electrodes 38P and 38N are formed on the exterior surface of the elongated cylindrical body member 35 and extend for almost the full length of the elongated cylinder. The strip-like electrodes 38P and 38N are radially spaced apart from one another and have applied thereto different polarity electric potentials from the internally mounted battery 21. If desired, additional circular plate-like electrodes 23 and 25 can be formed on the ends of the elongated cylindrical IUD body member. In other respects, the embodiment of FIG. 7 functions similar to that of the previously described embodiments of the invention.

FIG. 8 illustrates still another embodiment of the invention employing an elongated cylinder IUD body member 35 and circular conductive end plate electrodes 23 and 25. In the embodiment of the invention shown in FIG. 8, however, the cylindrical body itself is made up from a plurality of relatively thin, button-shaped batteries 39 of conventional, commercially available construction. The button-shaped batteries 39 are physically and electrically connected in series circuit relationship by means of a conductive adhesive 41 used to physically and electrically connect the positive terminal of each of the button-shaped batteries 39 to the negative terminal of its adjacent neighbor. The resultant composite structure then preferably is enclosed within an insulating coating of biologically inert material that is compatible with human tissue and fluids.

FIG. 9 of the drawings illustrates an embodiment of the invention wherein the battery itself, such as a AA or AAA battery of reduced diameter, comprises the IUD body member 35. The IUD body member 35 is provided with an exterior insulating coating that covers the longitudinal extent of the exterior surface of the battery, but leaves the end contact terminals 23 and 25 open and exposed. Such construction requires that the insulating coating and the end contact members 23 and 25 be fabricated from inert materials which are physically compatible with human flesh and fluids. Alternatively, the end electrode members 23 and 25 could be covered with electrically conductive enlarged electrode members such as the mushroom-shaped member 42 shown in FIG. 9 or spherically-shaped members or some other configuration which would better serve to hold the elongated cylindrical body member 35 in place within the uterus, and improve the electric field force distribution within the uterus.

FIG. 10 of the drawings portrays still a different embodiment of the invention wherein the electrified IUD body member is comprised by "coin"-shaped batteries having an upper electrode plate 43 and a lower electrode plate 44 with a solid electrolyte layer 45 sandwiched therebetween. The edge of the solid electrolyte 45 must be covered with an insulating coating that is electrically insulating and impervious to fluids and biologically inert so that it is physically compatible with human tissue and liquids. The two coin-shaped electrode members 43 and 44 while they must be conductive and exposed so as to serve as outer electrode members for electric field producing purposes also must be fabricated from conductive materials that are physically compatible with human tissue and liquids. In this embodiment of the invention, it is preferred that through-openings, such as shown at 46, be provided which pass entirely through both sides of the "coin"-shaped electrified IUD device to allow for drainage of fluids through the "coin"-shaped IUD while it is in place in the uterus of a female mammal. In other respects, the embodiment of the invention shown in FIG. 10 functions in substantially the same manner as those described earlier.

While only the embodiment of the invention illustrated in FIG. 1 has been shown with a cord or string 18 attached thereto for easy extraction of the electrified IUD from the uterus of a female mammal in which it has been placed for contraceptive purposes, it is believed obvious to one of ordinary skill in the art that such an extraction cord or string could be used with any one of the embodiments of the invention herein disclosed.

From the foregoing description it will be appreciated that the present invention provides a new and improved electrified intrauterine device that employs an electrified IUD body member, a self-contained electromotive force producing battery and external electrically conductive electrodes are provided for producing an electric field force within the uterus of a female mammal within whom the electrified IUD is implanted. The electric field forces thus induced within the uterus are effective to prevent migration of male sperm to any egg that might be present in the uterus thereby serving as an effective contraceptive for birth control purposes.

In addition to its function as an antispermicide as described above, it is believed that the electrified IUD also serves an antibacterial, an antifungal and anti-viral function as disclosed in the above-noted U.S. Pat. Nos. 4,616,640; 4,770,167 and U.S. patent application Ser. No. 141,132.

COMMERCIAL APPLICABILITY

An electrified intrauterine device is described which makes available a novel method and device for birth control employing the production of electric field forces within the uterus of a female mammal. The invention will find it greatest application in the field of family planning by the medical profession.

Having described several embodiments of a novel electrified IUD for use as a contraceptive for birth control purposes, it is obvious that other modifications and variations of the invention will be suggested to those skilled in the art in the light of the above teachings. It is therefore to be understood that changes may be made in the particular embodiments of the invention described which are within the full intended scope of the invention as defined by the appended claims.

What is claimed is:

1. An electrified intrauterine device (IUD) comprising an IUD body member fabricated from materials which are physiologically compatible with human tissue and fluids; said IUD body member being physically proportioned to be comfortably placed and retained within the uterus of a female mammal and does not exceed the dimensions of the uterus while being held in place in its expanded state,
    spaced-apart electrically conductive electrode means formed on the IUD body member from electrically conductive materials that are physiologically compatible with human tissue and fluids,
    self-contained electric battery means supported within sealed outer casing means of biologically inert material compatible with human tissue and fluids and capable of producing an electromotive force of known voltage and current rating,
    said battery means being of a size to be inserted and retained within the uterus of a female mammal, and
    electrically conductive interconnecting conductor means between respective opposite polarity terminals of the battery means and respective ones of the spaced-apart electrically conductive electrode means on the IUD body member whereby an electromotive field force can be established and maintained within the uterus of a female mammal in which the electrified IUD is inserted.

2. An electrified intrauterine device according to claim 1 wherein the battery means is contained within the IUD body member.

3. An electrified intrauterine device according to claim 1 wherein the IUD body member is formed from electrically insulating material and the spaced-apart electrode means are comprised by conductive pathways deposited or otherwise formed on the exterior of the IUD body member.

4. An electrified intrauterine device according to claim 3 wherein the battery means is contained within the IUD body member.

5. An electrified intrauterine device according to claim 4 further including a string or other similar strand of material which upon implantation of the device in the uterus of a female mammal extends out of the uterus and vagina so that the IUD body member readily can be extracted.

6. An electrified intrauterine device according to claim 5 wherein the IUD body member is T-shaped.

7. An electrified intrauterine device according to claim 6 wherein the IUD body member is in the shape of a seven (7-shaped).

8. An electrified intrauterine device according to claim 5 wherein the IUD body member is Z-shaped.

9. An electrified intrauterine device according to claim 5 wherein the IUD body member is in the shape of an elongated cylinder.

10. An electrified intrauterine device according to claim 9 wherein the spaced-apart electrically conductive electrodes extend longitudinally along the elongate axis of the cylindrically-shaped IUD body member.

11. An electrified intrauterine device according to claim 9 wherein the spaced-apart electrically conductive electrodes extend circumferentially around the elongate axis of the cylindrically-shaped IUD body member to form a plurality of axially extending, spaced-apart, parallel annular conductive rings.

12. An electrified intrauterine device according to claim 9 wherein the IUD body member is comprised by a plurality of thin, button-shaped electrolytic cells physically secured together in a series arrangement by electrically conductive adhesive to form a battery of desired voltage rating and physical length that also serves as the IUD body member.

13. An electrified intrauterine device according to claim 9 wherein the IUD body member is comprised by a conventional, elongated cylinder-type battery of desired voltage and current rating with exposed electrically conductive terminals at the respective ends thereof and with an exterior electrically insulating material covering the battery between the conductive terminal which is biologically compatible with human tissue and fluids.

14. An electrified intrauterine device according to claim 13 wherein the exposed electrically conductive terminals at the respective ends of the battery are mushroom-shaped.

15. An electrified intrauterine device according to claim 4 wherein the IUD body member comprises a relatively flat coin-shaped battery physically proportioned to fit within the uterus of a female mammal with the opposed flat sides of the coin-shaped battery being formed of electrically conductive material and comprising the opposite polarity electrodes of the intrauterine device.

16. An electrified intrauterine device according to claim 15 wherein the coin-shaped battery has a number of through-passages formed through the opposed flat surfaces to provide for drainage of fluids therethrough.

17. An electrified intrauterine device according to claim 1 further including a string or other similar strand of material which upon implantation of the device in the uterus of a female mammal extends out of the uterus and vagina so that the IUD body member readily can be extracted.

18. An electrified intrauterine device according to claim 1 wherein the IUD body member is T-shaped.

19. An electrified intrauterine device according to claim 1 wherein the IUD body member is in the shape of a seven (7-shaped).

20. An electrified intrauterine device according to claim 1 wherein the IUD body member is Z-shaped.

21. An electrified intrauterine device according to claim 1 wherein the IUD body member is in the shape of an elongated cylinder.

* * * * *